(12) United States Patent
Tanaka et al.

(10) Patent No.: US 8,372,655 B2
(45) Date of Patent: Feb. 12, 2013

(54) PLATE FOR MASS SPECTROMETRY, PROCESS FOR PREPARING THE SAME AND USE THEREOF

(75) Inventors: Kenji Tanaka, Tokyo (JP); Lyang-ja Lee, Tokyo (JP); Koji Munechika, Tokyo (JP); Hisashi Arikuni, Takarazuka (JP); Bungo Ochiai, Yonezawa (JP)

(73) Assignee: Protosera Inc., Tokyo (JP)

( * ) Notice: Subject to any disclaimer, the term of this patent is extended or adjusted under 35 U.S.C. 154(b) by 295 days.

(21) Appl. No.: 12/829,051

(22) Filed: Jul. 1, 2010

(65) Prior Publication Data
US 2010/0264029 A1 Oct. 21, 2010

Related U.S. Application Data

(60) Division of application No. 10/530,169, filed as application No. PCT/JP03/12711 on Oct. 3, 2003, now abandoned, which is a continuation-in-part of application No. 10/264,505, filed on Oct. 4, 2002, now abandoned, which is a continuation-in-part of
(Continued)

(30) Foreign Application Priority Data

Nov. 27, 2002 (JP) ................. 2002-344710

(51) Int. Cl.
| | |
|---|---|
| G01N 24/00 | (2006.01) |
| G01N 1/00 | (2006.01) |
| G01N 33/53 | (2006.01) |
| G01N 3/02 | (2006.01) |
| C12Q 1/68 | (2006.01) |
| B01L 9/00 | (2006.01) |

(52) U.S. Cl. ........ 436/174; 436/173; 436/807; 436/809; 422/50; 422/566; 73/856

(58) Field of Classification Search ................. 422/102; 436/86; 435/5
See application file for complete search history.

(56) References Cited

U.S. PATENT DOCUMENTS 3,324,069 A 6/1967 Koblitz et al.
(Continued)

FOREIGN PATENT DOCUMENTS

DE 40 17 805 A1 3/1991
GB 2 072 203 A 9/1981
(Continued)

OTHER PUBLICATIONS

Schreiner et al. (Ultraviolet matrix assisted laser desorption ionization-mass spectrometry of electroblotted proteins Electrophoresis, 1996, 17, 954-961).*

(Continued)

*Primary Examiner* — Dean Kwak
(74) *Attorney, Agent, or Firm* — Leydig, Voit & Mayer, Ltd.

(57) ABSTRACT

The present invention provides a plate for mass spectrometry comprising a support and a PVDF-containing coating (that is, a PVDF-deposited thin layer) thereon, and a method of preparing a plate for mass spectrometry, which comprises coating the support surface with PVDF. The present invention also provides a method of analyte identification comprising subjecting an analyte-containing sample to gel electrophoresis to separate the analyte, blotting the separated analyte from the gel to the above-described plate for mass spectrometry, and subjecting the plate to mass spectrometry, whereby the transferred analyte is analyzed.

10 Claims, 6 Drawing Sheets

Related U.S. Application Data application No. 10/038,918, filed on Jan. 3, 2002, now abandoned.

(60) Provisional application No. 60/272,981, filed on Mar. 2, 2001, provisional application No. 60/260,433, filed on Jan. 9, 2001.

U.S. PATENT DOCUMENTS

| | | |
|---|---|---|
| 4,789,734 A | 12/1988 | Pierschbacher |
| 5,130,201 A | 7/1992 | Yoshimura et al. |
| 5,585,275 A | 12/1996 | Hudson et al. |
| 5,595,636 A * | 1/1997 | Franzen ..................... 204/464 |
| 5,719,060 A | 2/1998 | Hutchens et al. |
| 5,894,063 A | 4/1999 | Hutchens et al. |
| 6,020,208 A | 2/2000 | Hutchens et al. |
| 6,027,942 A | 2/2000 | Hutchens et al. |
| 6,124,137 A | 9/2000 | Hutchens et al. |
| 6,225,047 B1 | 5/2001 | Hutchens et al. |
| 6,287,872 B1 | 9/2001 | Schurenberg et al. |
| 6,319,674 B1 | 11/2001 | Fulcrand et al. |
| 6,511,810 B2 | 1/2003 | Bi et al. |
| 6,528,320 B2 | 3/2003 | Hutchens et al. |
| 6,558,744 B2 | 5/2003 | Jarrell et al. |
| 6,761,902 B2 | 7/2004 | Sodroski et al. |
| 2001/0014461 A1 | 8/2001 | Hutchens et al. |
| 2001/0014479 A1 | 8/2001 | Hutchens et al. |
| 2001/0023074 A1 | 9/2001 | Hutchens et al. |
| 2002/0037517 A1 | 3/2002 | Hutchens et al. |
| 2002/0123043 A1 | 9/2002 | Hutchens et al. |
| 2002/0142343 A1 | 10/2002 | Hutchens et al. |
| 2002/0155509 A1 | 10/2002 | Hutchens et al. |
| 2002/0155620 A1 | 10/2002 | Hutchens et al. |
| 2002/0177242 A1 | 11/2002 | Hutchens et al. |
| 2003/0044843 A1 | 3/2003 | Tanaka et al. |

FOREIGN PATENT DOCUMENTS

| | | | |
|---|---|---|---|
| GB | 2 236 185 A | | 3/1991 |
| GB | 2235528 A | * | 3/1991 |
| GB | 2 292 699 A | | 3/1996 |
| GB | 2 312 782 A | | 11/1997 |
| JP | 07-118142 A2 | | 5/1995 |
| JP | 07-232399 A | | 9/1995 |
| JP | 07-267996 A2 | | 10/1995 |
| WO | WO 89/04322 A1 | | 5/1989 |
| WO | WO 94/28418 A1 | | 12/1994 |
| WO | WO 00/43791 A1 | | 6/2000 |
| WO | WO 00/45168 A1 | | 8/2000 |
| WO | WO 00/66265 A2 | | 11/2000 |
| WO | WO 00/67293 A1 | | 11/2000 |
| WO | WO 01/47947 A2 | | 7/2001 |
| WO | WO 01/49265 A1 | | 7/2001 |
| WO | WO 01/71326 A2 | | 9/2001 |
| WO | WO 02/056026 A1 | | 7/2002 |

OTHER PUBLICATIONS

Feld et al. (Comparative and Complementary Plasma Desorption Mass Spectrometry/Secondary Ion Mass Spectrometry Investigations of Polymer Materials, Anal. Chem. 1991, 63, 903-910).*

Kubono et al., Second-Harmonic Generation in Poly(vinylidene fluoride) Films Prepared by Vapor Deposition under an Electric Field, Jpn. J. Appl. Phys. vol. 31 (1992) L1195-L1197.*

Banerjee et al., "Proteoliposome as the Model for the Study of Membrane-Bound Enzymes and Transport Proteins," *Molecular and Cellular Biochemistry*, 50, 3-15 (1983).

Bienvenut et al., "Toward a Clinical Molecular Scanner for Proteome Research: Parallel Protein Chemical Processing before and during Western Blot," *Analytical Chemistry*, 71 (21), 4800-4807 (Nov. 1, 1999).

Binz et al., "A Molecular Scanner to Automate Proteomic Research and to Display Proteome Images," *Analytical Chemistry*, 71 (21), 4981-4988 (Nov. 1, 1999).

Chen et al., "Interaction of 11-*cis*-Retinol Dehydrogenase with the Chromophore of Retinal G Protein-coupled Receptor Opsin," *Journal of Biological Chemistry*, 276 (24), 21098-21104 (Jun. 15, 2001).

Dalençon et al., "Liposomes Bearing Platelet Proteins: A Model for Surface Functions Studies," *Biochimica et Biophysica Acta*, 1302, 241-248 (1996).

Echerskorn et al., "Analysis of Proteins by Direct-Scanning Infrared-MALDI Mass Spectrometry after 2D-PAGE Separation and Electroblotting," *Anal. Chem.*, 69, 2888-2892 (1997).

Feld et al., "Comparative and Complementary Plasma Desorption Mass Spectrometry / Secondary Ion Mass Spectrometry Investigations of Polymer Materials," *Anal. Chem.*, 63: 903-910 (1991).

Fulton et al., "Advanced multiplexed analysis with the FlowMetrix system," *Clinical Chemistry*, 43 (9), 1749-1756 (1997).

Fung et al., "Protein biochips for differential profiling," *Analytical Biotechnology*, 12, 65-69 (2001).

Gygi et al., "Quantitative analysis of complex protein mixtures using isotope-coded affinity tags," *Nature Biotechnology*, 17, 994-999 (Oct. 1999).

Han et al., "Quantum-dot-tagged microbeads for multiplexed optical coding of biomolecules," *Nature Biotechnology*, 19, 631-635 (Jul. 2001).

Hermann et al., "Proteome analysis of *Corynebacterium glutamicum*," *Electrophoresis*, 22, 1712-1723 (2001).

Heyse et al., *Biochemistry*, 37: 507-522 (1998).

Klarskov et al., "India Ink Staining After Sodium Dodecyl Sulfate Polyacrylamide Gel Electrophoresis and in Conjunction with Western Blots for Peptide Mapping by Matrix-Assisted Laser Desorption/Ionization Time-of-Flight Mass Spectrometry," *Rapid Communication in Mass Spectrometry*, 16, 35-42 (2002).

Loo et al., "Diffusive Transfer to Membranes as an Effective Interface Between Gel Electrophoresis and Mass Spectrometry," *International Journal of Mass Spectrometry and Ion Processes*, 169/170, 273-290 (1997).

Lueking et al., "Protein Microarrays for Gene Expression and Antibody Screening," *Analytical Biochemistry*, 270: 103-111 (1999).

Mirzabekov et al., "Paramagnetic Proteoliposomes Containing a Pure, Native, and Oriented Seven-Transmembrane Segment Protein, CCR5," *Nature Biotechnology*, 18, 649-654 (2000).

Okumura et al., "Transfer of Membrane Proteins from Human Platelets to Liposomal Fraction by Interaction with Liposomes Containing an Artificial Boundary Lipid," *Biochimica et Biophysica Acta*, 1194, 335-340 (1994).

Oshry et al., "Annexin-mediated membrane fusion of human neutrophil plasma membranes and phospholipid vesicles," *Biochimica et Biophysica Acta*, 1066, 239-244 (1991).

Parmar et al., "Incorporation of bacterial membrane proteins into liposomes: factors influencing protein reconstitution," *Biochimica et Biophysica Acta*, 1421, 77-90 (1999).

Schreiner et al., "Ultraviolet Matrix Assisted Laser Desorption Ionization-Mass Spectrometry of Electroblotted Proteins," *Electrophoresis*, 17, 954-961 (1996).

Shingles et al., "Production of Membrane Vesicles by Extrusion: Size Distribution, Enzyme Activity, and Orientation of Plasma Membrane and Chloroplast Inner-Envelope Membrane Vesicles," *Analytical Biochemistry*, 229, 92-98 (1995).

Simpson et al., "Proteomic analysis of the human colon carcinoma cell line (LIM 1215): Development of a membrane protein database," *Electrophoresis*, 21, 1707-1732 (2000).

Singh et al., "Gangliosides as Receptors for Biological Toxins: Development of Sensitive Fluoroimmunoassays Using Ganglioside-Bearing Liposomes," *Analytical Chemistry*, 72 (24), 6019-6024 (Dec. 15, 2000).

Suzuki et al., "Mechanism of Selective Release of Membrane Proteins from Human Erythrocytes in the Presence of Liposomes," *Archives of Biochemistry and Biophysics*, 379 (2), 344-352 (Jul. 15, 2000).

Traini et al., "Towards an Automated Approach for Protein Identification in Proteome Projects," *Electrophoresis*, 19, 1941-1949 (1998).

Zhou et al., "Solution and chip arrays in protein profiling," *TRENDS in Biotechnology*, 19 (10—Suppl.), S34-S39 (Oct. 2001).

Zhu et al., "Global Analysis of Protein Activities Using Proteome Chips," *Science*, 293, 2101-2105 (Sep. 14, 2001).

Wood et al., *Journal of Fluorine Chemistry*, 104(1): 63-71 (2000).

\* cited by examiner

PLATE FOR MASS SPECTROMETRY, PROCESS FOR PREPARING THE SAME AND USE THEREOF

CROSS-REFERENCE TO RELATED APPLICATIONS

This patent application is a divisional of U.S. patent application Ser. No. 10/530,169, filed Jul. 18, 2005, which is the U.S. national stage of International Patent Application PCT/JP03/12711, filed Oct. 3, 2003, which is a continuation-in-part of U.S. patent application Ser. No. 10/264,505, filed Oct. 4, 2002, now abandoned, which is a continuation-in-part of U.S. patent application Ser. No. 10/038,918, filed Jan. 3, 2002, now abandoned, which claims the benefit of U.S. Provisional Patent Application 60/272,981, filed Mar. 2, 2001, and U.S. Provisional Patent Application 60/260,433, filed Jan. 9, 2001, each of which is incorporated by reference.

TECHNICAL FIELD

The present invention relates to a new plate for mass spectrometry that enables proteome analysis in large amounts, with quickness, and at high sensitivity, a method of preparing the same, and use thereof.

BACKGROUND ART

Owing to the advances in fundamental research into drug innovation, including molecular biology and genomics (genome science), the circumstances of drug innovation have changed dramatically over these several years, and new approaches to drug innovation, represented by genome drug innovation, are being developed.

However, it remains impossible to predict protein functions (physiological actions) from the nucleotide sequences clarified by genomics; there is a post-genome need for the establishment of techniques that link genetic information to new drugs. As such, proteomics (protein analysis science) is drawing attention, which aims at isolating and identifying all proteins (reportedly more than 100,000 kinds) translated from the aforementioned nucleotide sequences, and assigning their functions.

Although proteome means all proteins that constitute a single organism in a narrow sense, it sometimes means, in a broad sense, all proteins contained in a histologically or anatomically specified portion of an organism, like all proteins in the cell fluid of a particular cell, all proteins contained in serum, all proteins contained in a particular tissue, and the like. In the present specification, this term is used in the broad sense, but it is evident that the complete assembly of proteomes in the broad sense is the proteome in the narrow sense.

In proteome analysis, a method combining two-dimensional electrophoresis and mass spectrometry has conventionally been used commonly, but the following problems remain unresolved. That is, in the conventional method, the migration gel must be divided into fractions, from each of which proteins must be extracted with a special solution, before the sample is subjected to mass spectrometry after migration. Due to the long time taken and the requirement of painstaking operation in multiple stages, measuring time shortening, apparatus size reduction, screening of a large number of analytes, and whole-apparatus automation have been extremely difficult.

Furthermore, there is another problem of what is called "low-abundance proteins". In yeast, for example, only 100 genes produce 50% of the total protein weight of the yeast. This means that the remaining 50% proteins are products of thousands of genes. A large amount of low-abundance proteins contains a large amount of proteins that are most important to the body, such as regulatory proteins and signal transmission proteins, including receptors. However, the situation with the conventional method is such that the large number and trace amount of protein samples separated by electrophoresis cannot be recovered.

In an attempt to overcome these limitations in the combined technology of electrophoresis and mass spectrometry, and to clarify protein-protein interactions, a variety of efforts are now being made. For example, the isotope-coded affinity tag method (ICAT: isotope-coded affinity tag; *Nat. Biotech.*, 17: 994-999 (1999)), the two-hybrid system in yeast, BTA-MS-MS, the protein array method (solution, chip; *Trends Biotechnol.*, 19: S34-39 (2001)), peptidomics by LC-MS-MS, and the like are available. In particular, as examples of the protein array method, the solid phase protein array method (chip method; *Curr. Opin. Biotechnol.*, 12: 65-69 (2001)), the liquid phase array method (fluorescence-encoded beads; *Clin. Chem.*, 43: 1749-1756 (1997); *Nat. Biotech.*, 19: 631-635 (2001); barcoded nanoparticles; *Trends Biotechnol.* (2001), ibidem), wherein information has been incorporated in nano-particles, and the like can be mentioned.

Meantime, the present inventors have proposed a method of proteome analysis that enables simultaneous analysis of membrane proteins and compounds capable of interacting therewith by grouping them (WO 02/56026).

Aside from such improvements in measuring methods (systems), there are some reports of attempts for improvements in the field of protein mass spectrometry, though they are not intended for proteome analysis, or are technically difficult to apply to proteome analysis. Methods have been reported, which comprise blotting proteins separated by electrophoresis to a polyvinylidene difluoride (PVDF) membrane, and taking measurements with the membrane immobilized to a stainless steel plate for MALDI type mass spectrometry using a double-coated tape (*Electrophoresis*, 17: 954-961 (1996)), a frame (*Anal. Chem.*, 69: 2888-2892 (1997)) or grease (*Anal. Chem.*, 71: 4800-4807 (1999); *Anal. Chem.*, 71: 4981-4988 (1999); WO 00/45168). These methods are faulty in that not only the procedures are painstaking due to immobilization of the PVDF membrane to the plate for mass spectrometry in the midst of measurement, but also the background is high and the relative peak intensity is extremely low, so that they are unsuitable to proteome analysis, which requires high detection sensitivity.

Also, a method comprising blotting a gel after electrophoresis directly to a matrix-coated plate for mass spectrometry and conducting mass spectrometry, and a method comprising electrically blotting a protein to a PVDF membrane for blotting, and then diffusion-blotting the protein to a matrix-coated plate for mass spectrometry, have been reported (U.S. Pat. No. 5,595,636). However, in these methods, when electrical blotting is used, there is concern that the matrix dissolves in the blotting buffer during blotting and measurements themselves become impossible. On the other hand, when diffusion blotting is used, the blotting efficiency is low so that the detection sensitivity is insufficient particularly to blotting low-abundance proteins to a plate for mass spectrometry.

Furthermore, a method based on an improvement of the above-described method has been reported, which comprises applying a mixture of nitrocellulose (a membrane component for blotting use) and a matrix to a plate for mass spectrometry as (GB 2312782 A). However, even this method cannot be said to have completely resolved the problems, in the case of electrical blotting or diffusion blotting.

As plates for mass spectrometry, commonly used aluminum or stainless steel plates, as well as improvements thereof, such as plates for mass spectrometry coated with silica, or having a hydrophobic group added thereto, are commercially available (manufactured by Ciphergen, WO 94/28418). However, even these technologies and products do not always meet the research and development needs for conducting proteome analysis in large amounts, with quickness, and at high sensitivity.

An object of the present invention is to introduce a new technology to the conventional method of proteome analysis based on a combination of electrophoresis and mass spectrometry. Specifically, the object of the present invention is to provide a technology that enables the conduct of proteome analysis in large amounts, with quickness, and at high sensitivity.

DISCLOSURE OF THE INVENTION

The present invention is based on the discovery that a plate for mass spectrometry prepared by coating a substrate with PVDF to form a thin layer of PVDF on the substrate offers dramatically improved mass spectrometry detection sensitivity and accuracy compared to those of one wherein PVDF is immobilized on a substrate in the form of a membrane. Also, because such a plate for mass spectrometry does not contain a matrix at the time of blotting, it is additionally advantageous in that the matrix does not dissolve even in electrical blotting.

Accordingly, the present invention relates to:
1) a plate for mass spectrometry comprising a support and a PVDF-containing coating thereon;
2) a method of preparing a plate for mass spectrometry, which comprises coating the support surface with PVDF; and
3) a method of identifying an analyte, which comprises subjecting an analyte-containing sample to gel electrophoresis to separate the analyte, blotting the separated analyte to a plate for mass spectrometry obtained by the method of 1) above or 2) above, and subjecting the blotted analyte to mass spectrometry.

Further objectives and features of the present invention and the effect of the present invention will be evident through the following detailed description of the invention.

BRIEF DESCRIPTION OF THE DRAWINGS

FIG. 5 shows the results of an analysis of the protein-protein interaction between a protein (SCUPA) electrically blotted using the plate for mass spectrometry of the present invention and an antibody that specifically reacts thereto (anti-SCUPA antibody) by mass spectrometry. The horizontal axis indicates molecular weight, and the vertical axis indicates relative intensity. The numerical symbols in the Figure indicate the molecular weights of the peaks. FIG. 5B shows the results obtained using the anti-SCUPA antibody alone.

BEST MODES FOR EMBODYING THE INVENTION

Plate for Mass Spectrometry

Figure 1:
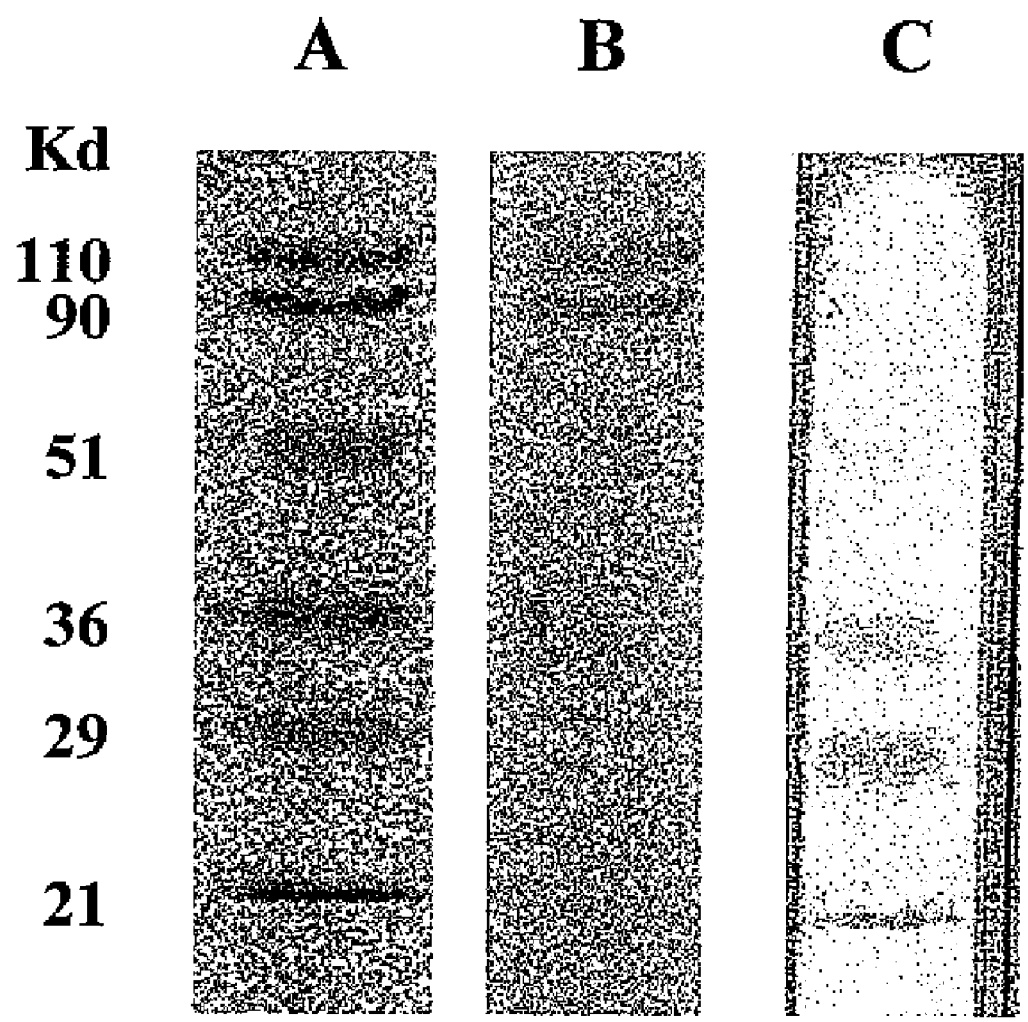
FIG. 1 shows the extent of electrical blotting from the migration gel to the plate for mass spectrometry. A indicates the migration gel (before blotting), B indicates the migration gel (after blotting), and C indicates the plate for mass spectrometry of the present invention (after blotting). The numerical symbols on the left end show the molecular weights of the proteins corresponding to the bands. It is shown that nearly all portions of the proteins in the gel migrate to the plate for mass spectrometry due to electrical blotting in the case of some proteins.

The plate for mass spectrometry of the present invention has a coating (thin layer) containing polyvinylidene difluoride (PVDF) on a support (basic structure). The material for the support is not subject to limitation, as long as it is one in common use in plates for mass spectrometry. As examples, insulators (glass, ceramics, plastics/resins and the like), metals (aluminum, stainless steel and the like), electroconductive polymers, complexes thereof and the like can be mentioned. Preferably, an aluminum plate is used.

The shape of the plate for mass spectrometry of the present invention is designed to fit particularly to the sample inlet of the mass spectrometer used. For example, a cluster type plate for mass spectrometry previously notched to enable easy separation of individual segments so that each fits to the sample inlet of the mass analyze after a protein is blotted to an assembly type plate for mass spectrometry adapted to the size of the gel after electrophoresis, and the like can be mentioned, which, however, are not to be construed as limiting the invention.

In the present invention, "PVDF-containing coating" refers to a thin layer formed by depositing PVDF molecules in dispersion on the support, rather than to a layer prepared by overlaying a previously molded structure on the support as with a conventionally known PVDF membrane. Although the mode of PVDF deposition is not subject to limitation, the means mentioned as examples in the method for preparing a plate for mass spectrometry which is described below are preferably used.

The thickness of the thin layer can be appropriately chosen, as long as it does not adversely affect protein blotting efficiency and mass spectrometry measuring sensitivity and the like, and is, for example, about 0.1 to about 1000 μm, preferably about 1 to about 300 μm.

A method for Preparing a Plate for Mass Spectrometry

The plate for mass spectrometry of the present invention is prepared by coating the support surface with PVDF. As preferable examples of the means of coating, painting, spraying, vapor deposition, immersion, printing, sputtering and the like can be mentioned.

In the case of "painting", PVDF dissolved in an appropriate solvent, for example, an organic solvent such as dimethyl formamide (DMF), at an appropriate concentration (for example, about 1 to about 100 mg/mL) (hereinafter referred to as "PVDF-containing solution"), can be painted to the support (basic structure, substrate) using an appropriate tool such as a brush.

In the case of "spraying", a PVDF-containing solution prepared in the same manner as above may be sprayed from a sprayer so that PVDF is uniformly deposited on the support.

In the case of "vapor deposition", a thin layer of PVDF can be formed on the support surface by heating and vaporizing PVDF (may be solid or solution) in a vacuum chamber containing the support using an ordinary vacuum vapor deposition apparatus for preparation of organic thin membranes.

In the case of "immersion", the support may be immersed in a PVDF-containing solution prepared in the same manner as above.

In the case of "printing", various commonly usable printing techhnologies can be appropriately chosen and utilized according to the material of the support; for example, screen printing and the like can be preferably used.

In the case of "sputtering", a thin layer can be formed, for example, by applying a direct current high voltage between the support and PVDF while an inert gas (e.g., Ar gas and the like) is introduced into a vacuum, and colliding the ionized gas to the PVDF to allow the sputtered PVDF molecules to deposit on the support.

A coating may be applied to all faces of the support, and may be applied only to one face subjected to mass spectrometry.

PVDF can be used appropriately in a preferred form according to the coating means; for example, PVDF can be applied to the support in the form of a PVDF-containing solution, PVDF-containing vapor, PVDF solid molecules and the like, and it is preferably applied in the form of a PVDF-containing solution. "Apply" means that PVDF is brought into contact with the support so that it remains and accumulates on the support after contact. The amount applied is not subject to limitation; as an example of the amount of PVDF, about 1 to about 100 μg/cm$^2$ can be mentioned. After application, the solvent is removed by spontaneous drying, vacuum drying and the like.

The support (basic structure, substrate) in the plate for mass spectrometry of the present invention may have the surface thereof previously modified (processed) by an appropriate physical or chemical technique before being coated with PVDF. Specifically, techniques such as plate surface polishing, abrasion, acid treatment, alkali treatment, and glass treatment (tetramethoxysilane and the like) can be mentioned as examples.

The plate for mass spectrometry of the present invention is excellent in stability. That is, the plate for mass spectrometry of the present invention is characterized in that the adhesive surface does not peel even under such conditions as immersion in an aqueous solution having a pH of 2 to 10, or containing various salts, a solvent such as methanol or acetonitrile, or a mixed solvent thereof, electrical loading, repeated cycles of wetting and drying, and a highly vacuum state.

Use of the Plate

A. Identification of Proteins and the Like

Using the plate for mass spectrometry of the present invention, various compounds, including proteins, can be identified. That is, by subjecting a sample containing an analyte (e.g.: protein, nucleic acid, oligonucleotide, saccharide, oligosaccharide, cell membrane receptor agonist or antagonist, toxin, virus epitope, hormone, peptide, enzyme, enzyme substrate or inhibitor, cofactor, drug, lectin, antibody and the like) to an electrophoresis (e.g.: polyacrylamide gel electrophoresis) to separate the analyte, blotting the separated analyte to the plate for mass spectrometry of the present invention, and analyzing the blotted analyte by mass spectrometry, the analyte is identified (from information on the molecular weight thereof).

Analyte-Containing Sample

The analyte-containing sample may be prepared from a (biological) material using any known technique. Here, as examples of the (biological) material, cells or tissues of optionally chosen organisms such as animals, plants and microorganisms, or extracellular fluids (for example, blood, plasma, urine, bone marrow fluid, ascites fluid and the like), intracellular fluids, fluids in cell small granules, and the like can be mentioned. Also, cell culture broths, culture broths obtained by gene recombination, and the like are also included.

To prepare an analyte-containing sample subjected to electrophoresis, a known method is used. For example, in the case of a protein-containing sample, a soluble fraction can be obtained by collecting a centrifugal supernatant after target cells are homogenized in an appropriate buffer in the presence of various protease inhibitors, or after the cells are suspended using a cell disruption apparatus such as Polytron, or after the cells are disrupted by hypo-osmotic shock, or after the cell membranes are disrupted by sonication. Also, the obtained precipitate (insoluble) fraction can be used as after being solubilized using a surfactant or a protein denaturant.

Electrophoresis

This is a step wherein the analyte in the sample is separated (developed on gel) by electrophoresis. The electrophoresis apparatus used can be a known one. A commercial product may be used. According to the purpose, any of one-dimensional gel electrophoresis and two-dimensional gel electrophoresis can be used. In two-dimensional gel electrophoresis, one-dimensional migration is based on separation according to analyte isoelectric point, and two-dimensional migration on separation according to analyte molecular weight. The size of the gel used for electrophoresis is not subject to limitation. Although 10 cm×10 cm is a commonly used size, 20 cm ×20 cm or other sizes can be used if necessary. Also, although the material of the gel is basically polyacrylamide, utilization of other media such as agarose gel and cellulose acetate membrane is also possible depending on the purpose. For the concentration of the gel, both a uniform concentration and a gradient concentration can be used.

Blotting

This is a step wherein the analyte separated by gel electrophoresis is transferred from the gel to the plate for mass spectrometry of the present invention. As the blotting apparatus, a known one can be used. A commercial product may be used. The method of blotting is known per se. The analyte developed on the gel after migration is transferred to the plate for mass spectrometry by various methods (diffusion, electrical force and others). This step is generally called blotting. Diffusion blotting, electrical blotting and the like can be mentioned. Electrical blotting is particularly preferable.

As the buffer used at the time of electrical blotting, it is preferable to use one of a pH of 7 to 9 and of a low-salt concentration. Specifically, a Tris buffer, a phosphate buffer, a borate buffer, an acetate buffer and the like can be mentioned as examples. As the Tris buffer, Tris/glycine/methanol buffer, SDS-Tris-Tricine buffer and the like can be mentioned; as the phosphate buffer, ACN/NaCl/isotonic phosphate buffer, sodium phosphate/ACN and the like can be mentioned; as the borate buffer, sodium borate-hydrochloride buffer, Tris-borate salt/EDTA, borate salt/ACN and the like can be mentioned; as the acetate buffer, Tris-acetate salt/EDTA and the like can be mentioned. Preferably, the buffer is Tris/glycine/methanol buffer or sodium borate-hydrochloride buffer. As examples of the composition of the Tris/glycine/methanol buffer, 10-15 mM Tris, 70-120 mM glycine, 7-13% methanol or so can be mentioned. As examples of the composition of the sodium borate-hydrochloride buffer, 5-20 mM sodium borate or so can be mentioned.

Also, after the blotting, a reagent called matrix can be added to absorb laser, and to promote the ionization of analyte molecules through energy transfer, so that the subsequent mass spectrometry (by the MALDI method) is effected. As the matrix, one known in the field of mass spectrometry can be used. For example, sinapinic acid (SPA (=3,5-dimethoxy-4-hydoroxycinammic acid)), indoleacrylic acid (IAA), 2,5-dihydroxybenzoic acid (DHB), α-cyano-4-hydroxycinammic acid (CHCA) and the like can be mentioned, which, however, are not to be construed as limiting the matrix. Preferably, the matrix is DHB or CHCA. In the case of CHCA, it is preferable to add one of at least 21% saturation concentration. Specifically, those of 21 to 100% saturation concentration, preferably those of 40 to 100% saturation concentration, and particularly preferably those of 50 to 100% saturation concentration can be mentioned.

Mass Spectrometry

This is a step wherein the analyte is identified (from information on molecular weight) by analyzing the analyte blotted to the plate for mass spectrometry of the present invention by mass spectrometry. The mass spectrometer is an apparatus that measures and detects the molecular weight of a substance by ionizing a gaseous sample, thereafter bringing molecules or molecule fragments thereof into an electromagnetic field, separating the substance by mass number/charge number based on the transfer status thereof, and determining the spectrum of the substance. It is possible to use mass spectrometers based on the principles of the MALDI-TOFMS method, which is a combination of matrix-aided laser deionization (MALDI), comprising mixing and drying a sample and a laser-absorbing matrix to cause crystallization, subjecting the crystal to ionization by energy transfer from the matrix and instantaneous heating by laser irradiation, and introducing the ionized analyte into a vacuum, and time-of-flight mass spectrometry (TOFMS), comprising analyzing mass number by sample molecule ion time-of-flight differences due to initial acceleration; the method comprising placing a single analyte on one droplet and electrically ionizing the analyte directly from the liquid; the nano-electrospray mass spectrometry (nano-ESMS) method, comprising electrically spraying a sample solution into the atmosphere to vaporize individual analyte polyvalent ions in an unfolded state, and the like.

The method of subjecting an analyte on the plate for mass spectrometry of the present invention to mass spectrometry is known per se.

Also, for fully automating proteome analysis according to the present invention, it is possible to analyze all analytes developed one-dimensionally or two-dimensionally by electrophoresis by moving the laser exit or, conversely, the stand with the plate for mass spectrometry on, toward one-dimensional or two-dimensional directions, and performing continuous full-surface scans (in the intermittent scan method, there remain analytes not irradiated with laser, that is, not analyzed). Combining this method with the intermittent scan method makes it possible to mount 96 kinds of samples dispensed to a 96-well plate as a whole to a plate for mass spectrometry (96 kinds of samples arranged at constant intervals in a rectangular chip), and subject the samples as is to mass spectrometry.

B. Identification of a Group of Analytes

According to the present invention, it is possible to analyze an assembly of a plurality of kinds of analytes (a group of analytes) at one time. That is, the analyte-containing sample prepared from the above-described various biological materials usually contains many kinds and a wide variety of analytes. By separating such a group of analytes by one-dimensional or two-dimensional gel electrophoresis, and blotting the group of analytes separated and developed on the gel to, for example, a plate for mass spectrometry of the present invention of a size that fits to the migration gel (preferably a cluster type plate for mass spectrometry having perforated lines made previously to enable easy separation of each piece so that it fits to the sample inlet of the mass spectrometer after blotting), it is possible to fractionate all, as a rule, analytes contained in the analyte-containing sample (proteomes if the analytes are proteins) to respective positions and blotting them to the plate for mass spectrometry. By measuring these a group of analytes using the above-described continuous scan type mass spectrometer, the blotted a group of analytes can be identified at one time.

C. Identification of Analyte Complex

According to the present invention, the linkage of an analyte and one that has affinity for (interacts with) the analyte can be analyzed at one time. That is, by separating the analyte by electrophoresis, blotting the separated analyte to the plate for mass spectrometry of the present invention, thereafter adding a sample containing a compound that has affinity for (interacts with) the analyte (for example, peptide, protein, nucleic acid, non-peptide compound, synthetic compound, fermentation product, cell extract, plant extract, animal tissue extract, cell membrane fraction, organelle membrane fraction and the like) to form a complex on the plate, and subjecting the formed complex to mass spectrometry, the blotted analyte, a compound that has affinity (interacts with) the analyte, and/or a complex thereof is identified (from information on molecular weight).

To describe the present invention in more detail, Examples are given below, which examples, however, are not to be construed as limiting the present invention.

EXAMPLE 1

Preparation of Plate for Mass Spectrometry

An aluminum basic structure (aluminum plate) prepared to fit to the inlet of the plate for mass spectrometry of the ProteinChip System (manufactured by Ciphergen) was immersed in 1% tetramethoxysilane/1% acetic acid solution and air-dried, after which it was burned (130° C., 3 hours). To this plate, polyvinylidene difluoride (PVDF) dissolved in dimethylformamide (DMF) to 10 mg/mL was applied. The plate for mass spectrometry prepared was tabular and 78 mm×8 mm×2 mm in size, and had a white surface.

This plate for mass spectrometry suffered absolutely no chemical, electrical, mechanical or physical changes such as cracking, peeling, damage and discoloration, in the subsequent steps such as pretreatment by immersion in an organic solvent, contact with electrophoresis gel, electrical blotting in various buffers, and high vacuums during subsequent matrix application and drying and mass spectrometry.

Using this plate for mass spectrometry, the following investigation was conducted.

EXAMPLE 2

Electrical Blotting of Protein to Plate for Mass Spectrometry

After a prestained molecular weight marker (manufactured by Bio-Rad) was subjected to 12% SDS-polyacrylamide gel electrophoresis, the protein on the gel was electrically blotted to the plate for mass spectrometry prepared in Example 1 at 90 mA for 3 hours in 12.5 mM Tris/96 mM glycine/10% methanol buffer. As a result, although small amounts of prestained proteins having molecular weights of 90,000 and 110,000 remained in the polyacrylamide gel after blotting (FIG. 1B), all proteins were efficiently blotted to the plate for mass spectrometry of the present invention (FIG. 1C).

EXAMPLE 3

Mass Spectrometry for Protein Blotted to Plate for Mass Spectrometry

After a sample (protein mixture) was subjected to 12% SDS-polyacrylamide gel electrophoresis, the gel was brought into direct contact with the plate for mass spectrometry of Example 1, the protein separated by electrophoresis was electrically blotted to the plate for mass spectrometry prepared in Example 1, and this plate for mass spectrometry was immediately placed in a mass spectrometer and measured. Using 2,5-dihydroxybenzoic acid (DHB; 75 mg/mL ethanol solution) as the matrix, and using the ProteinChip System (described above) as the measuring apparatus, measurements were taken under the conditions of a detector voltage of 1800 V, a detector sensitivity of 8, and a laser intensity of 280. For mass calibration, external calibration was conducted using myoglobin (derived from equine muscle), GAPDH (derived from rabbit), and albumin (derived from bovine serum). In this experiment, two kinds of proteins, namely a single chain urinary plasminogen activator (SCUPA) and human serum albumin (HSA), were used as the protein mixture, and 4 μg of the protein mixture was twice electrophoresed tandem to 12% SDS-polyacrylamide gel under reducing conditions. That is, an initial sample was added, and electrophoresis was performed at 30 mA for 40 minutes, after which the electricity was broken, the same sample was again added to the same lane, and electrophoresis was further performed at 30 mA for 23 minutes. After migration, the gel was cut for each migration lane, and further cut at a position 39 mm from the addition site on the upper face of the gel, after which the two pieces of the gel were placed with their upper faces in contact with each other, and thereafter brought into contact with the plate for mass spectrometry (FIG. 2A). At this time, the migration samples were arranged in the order of SCUPA, HSA, SCUPA, HSA, HSA, SCUPA, HSA and SCUPA, and four bands of each protein, eight bands in total, were blotted to the plate for mass spectrometry.

Figure 2B:
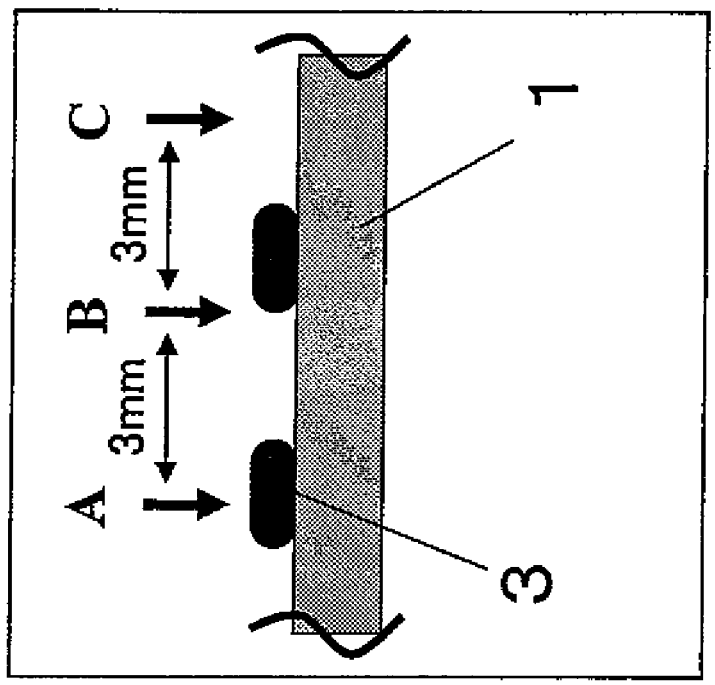
FIG. 2 shows the positional relationship between a migration gel and a plate for mass spectrometry (FIG. 2A) and differences in the quantity of laser received by the migrated protein on the plate (FIG. 2B). In the figures, 1, 2 and 3 indicate a plate for mass spectrometry, a migration gel, and a protein, respectively. Also, A, B and C indicate maximum light quantity, small light quantity, and zero light quantity, respectively.
Figure 2A:
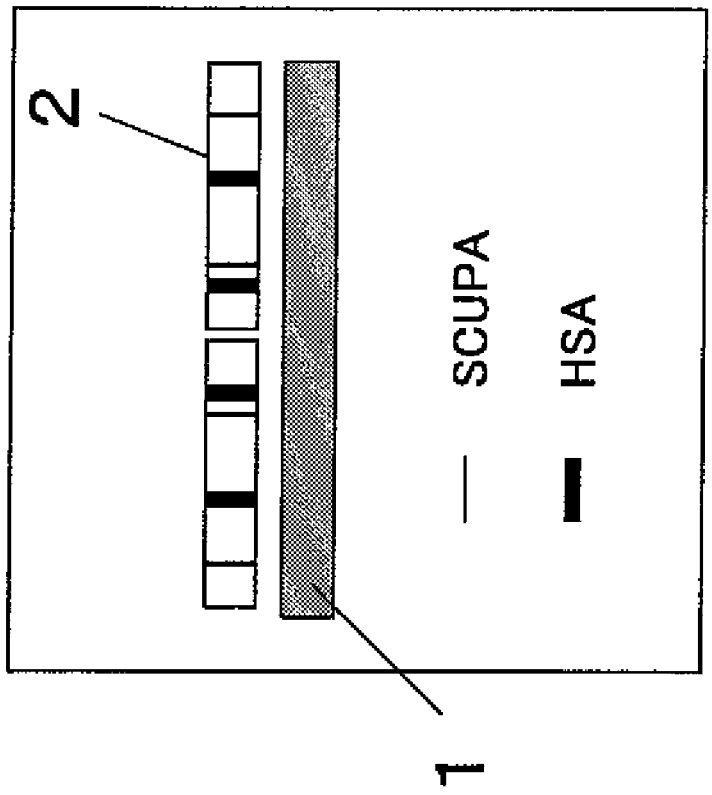
Figure 3A:
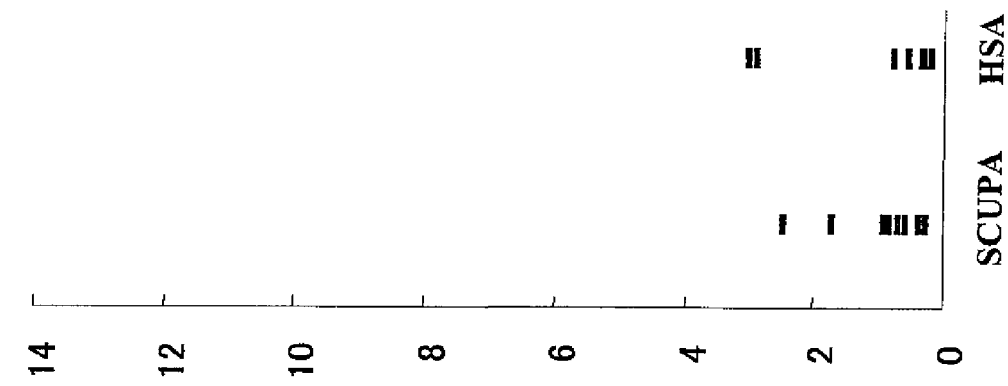
FIG. 3 shows the relative intensities of mass spectrometry peaks obtained using the plate for mass spectrometry of the present invention (FIG. 3A), an aluminum plate (FIG. 3B), and a ProteinChip array (H4, FIG. 3C).
Figure 3B:
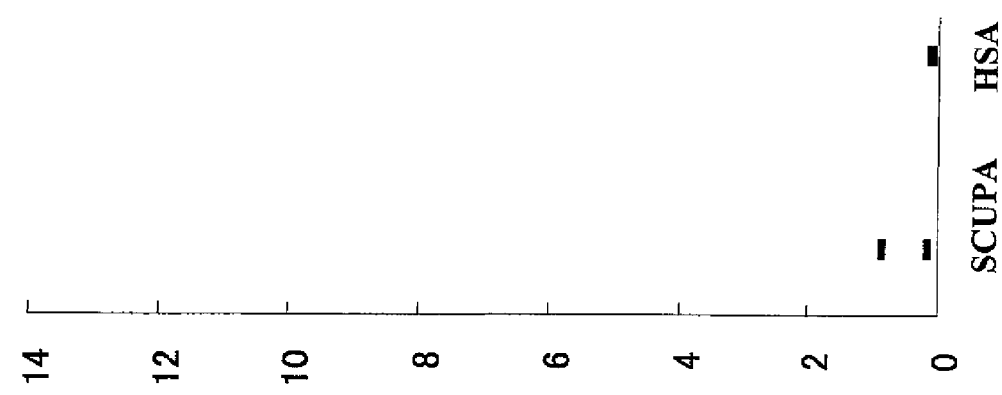

Because the mass spectrometer used irradiates laser to a single plate for mass spectrometry not continuously but at 24 equally spaced points, there occurs a case of no-exposure to laser, a case of partial exposure, and a case of full exposure, depending on the position of the blotted protein on the plate for mass spectrometry (FIG. 2B). To increase the probability of the greatest exposure to laser and hence the highest peak intensity with this limitation in the analytical apparatus, a mode was designed to blot each model protein to four different positions on the plate for mass spectrometry by the technique described above. As a result, even when proteins of theoretically the same mass were blotted, the heights of the peaks obtained from mass spectrometry were variable (FIG. 3). Hence, in this experiment, a discussion was made assuming the peak of the largest relative intensity out of the plurality of peaks obtained to be the value closest to the true value of complete exposure to the laser.

The plate for mass spectrometry was previously immersed in methanol and equilibrated with a blotting buffer (10 mM sodium borate buffer, pH 8.0), after which it was subjected to electric blotting at 90 mA for 2 hours. Subsequently, mass spectrometry was conducted and relative peak intensity was measured. For reference controls, other experiments were conducted in the same manner but using an ordinary non-PVDF-coated aluminum plate and an aluminum plate having a hexadecyl group introduced thereto (ProteinChip array, manufactured by Ciphergen, H4). The results are shown in FIG. 3 and FIG. 4.

Figure 3C:
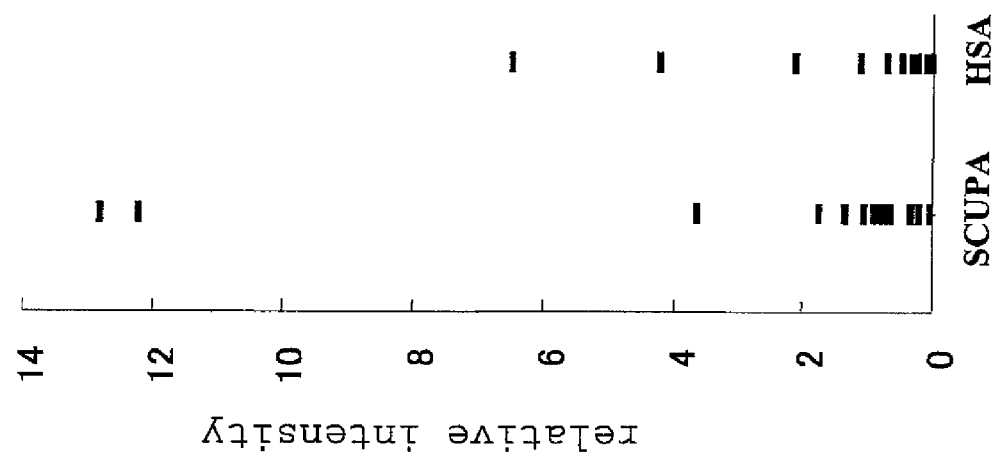
Figure 4A:
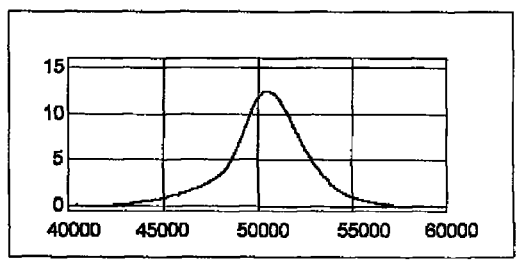
FIGS. 4A and B show the results for SCUPA, and FIGS. 4C and D for HSA. Also, FIGS. 4A and C show the case using the plate for mass spectrometry of the present invention, and FIGS. 4B and D show the case using the aluminum plate.
Figure 4B:
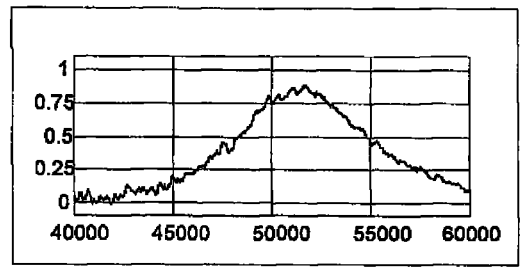
FIG. 4 shows the mass spectrometry spectra (peak images) of SCUPA and HSA obtained using the plate for mass spectrometry of the present invention or an aluminum plate. The horizontal axis indicates molecular weight, and the vertical axis indicates relative intensity.
Figure 4C:
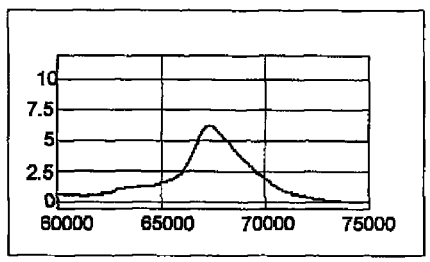
Figure 4D:
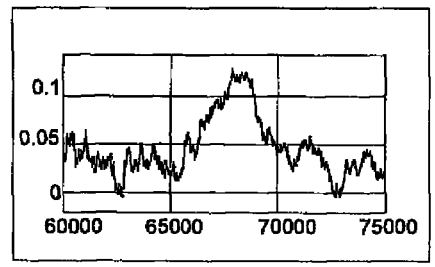

In the case of SCUPA, the relative peak intensity for the plate for mass spectrometry of the present invention (FIG. 3A) was 12.31, a level 14 times as high as the value of the ordinary aluminum plate (FIG. 3B) (0.87). Making a similar comparison for HSA, the relative peak intensity for this plate for mass spectrometry was 49 times (6.26:0.129) as high as the value of the aluminum plate. Also, the plate for mass spectrometry produced 2 times to 4 times as high relative peak intensity as those from H4 (FIG. 3C). Furthermore, the plate for mass spectrometry of the present invention (FIGS. 4A and C) produced more distinct spectra than those from the aluminum plate (FIGS. 4B and D). From these results, it was found that by using the plate for mass spectrometry of the present invention, a plurality of kinds of proteins, after separation by electrophoresis, could be analyzed by mass spectrometry with quickness and at high sensitivity at one time.

EXAMPLE 4

Analysis of Interaction Between Electrically Blotted Protein and Binding Protein After Electrophoresis Separation As an example application of the plate for mass spectrometry of the present invention, an investigation was conducted on the binding of a protein blotted to a plate for mass spectrometry and a protein capable of interacting therewith, and on the identification of the protein complex thereof by subsequent mass spectrometry. As the materials, SCUPA and an antibody thereof (anti-SCUPA antibody) were used.

After SCUPA (4 μg) was added to 12% SDS-polyacrylamide gel, electrophoresis was performed for 1 hour. After migration, the gel was cut, and the SCUPA on the gel was electrically blotted to the plate for mass spectrometry prepared in Example 1, in the same manner as Example 3. After the SCUPA-blotted plate for mass spectrometry was blocked, an antiserum (crudely purified using ammonium sulfate, and containing anti-SCUPA antibody) was added, and an overnight reaction was carried out. After completion of the reaction, the plate was washed with PBS buffer, a matrix was added, and mass spectrometry was conducted. The results are shown in FIG. 5.

Figure 5A:
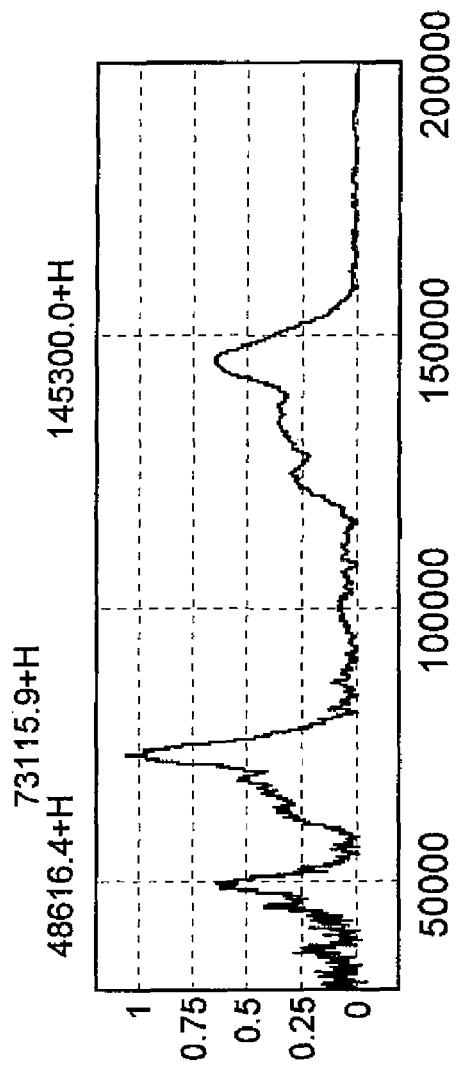
FIG. 5A shows the interaction between the separated and blotted SCUPA and the anti-SCUPA antibody. Also.
Figure 5A:
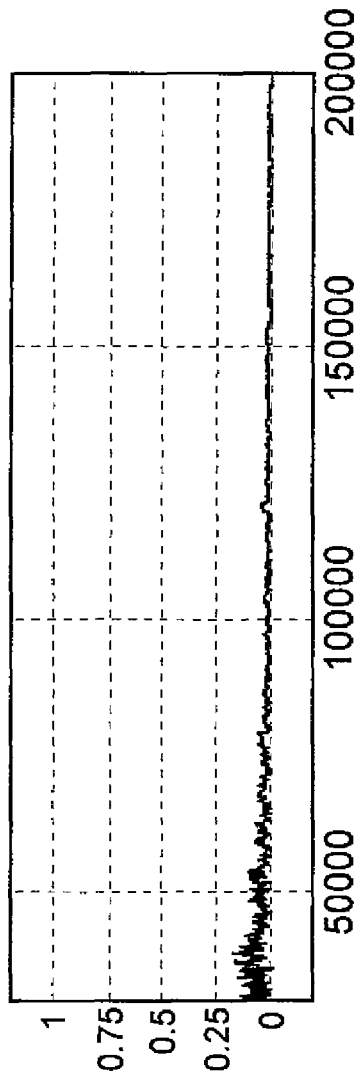

The SCUPA blotted to the plate for mass spectrometry after electrophoresis produced a peak at 48,616, and the peak of the anti-SCUPA antibody that interacted with the SCUPA immobilized on the same plate was observed at 145,300 (73,115 assigned to the divalent ion of the same antibody) (FIG. 5A). Also, in the SCUPA-free gel as the control, no peaks were observed in this plate for mass spectrometry, despite that similar procedures such as electrical blotting, blocking, addition of anti-SCUPA antibody, and washing with PBS were followed (FIG. 5B).

From the above results, which show that after electrophoresis separation, the SCUPA blotted to this plate for mass spectrometry retained activity to bind to a protein capable of interacting therewith (anti-SCUPA antibody), and that the molecular weights of both the blotted protein and the protein interacting therewith were actually determined at one time, resulting in the identification of both molecular species, it was demonstrated that detection of the protein-protein complex on this plate for mass spectrometry and identification of the complex produced on this plate for mass spectrometry are possible.

COMPARATIVE EXAMPLE 1

Blotting to PVDF Membrane and Mass Spectrometry

On 12% SDS-polyacrylamide gel, a mixture of 4 µg of each of two kinds of proteins, namely SCUPA and HSA, was twice electrophoresed tandem under reducing conditions. An initial sample was added, and electrophoresis was performed at 30 mA for 40 minutes, after which the electricity was broken, the same sample was again added to the same lane, and electrophoresis was further performed at 30 mA for 23 minutes. After migration, the gel was cut for each migration lane, and further cut at a position 39 mm from the addition site on the upper face of the gel; as illustrated in FIG. 2A, the two pieces of the gel were placed with their upper faces in contact with each other, and a 78 mm×8 mm cut PVDF membrane was placed on the gels, and electrical blotting was conducted in 10 mM sodium borate buffer (pH 8.0) at 90 mA for 2 hours. After completion of blotting, the PVDF membrane was washed with PBS, rinsed with distilled water, dried, and applied to an aluminum plate using a transparent a double-coated tape (manufactured by Sumitomo 3M Ltd.). A matrix (DHB) was added thereto, and mass spectrometry was conducted using the ProteinChip System (described above).

Figure 6A:
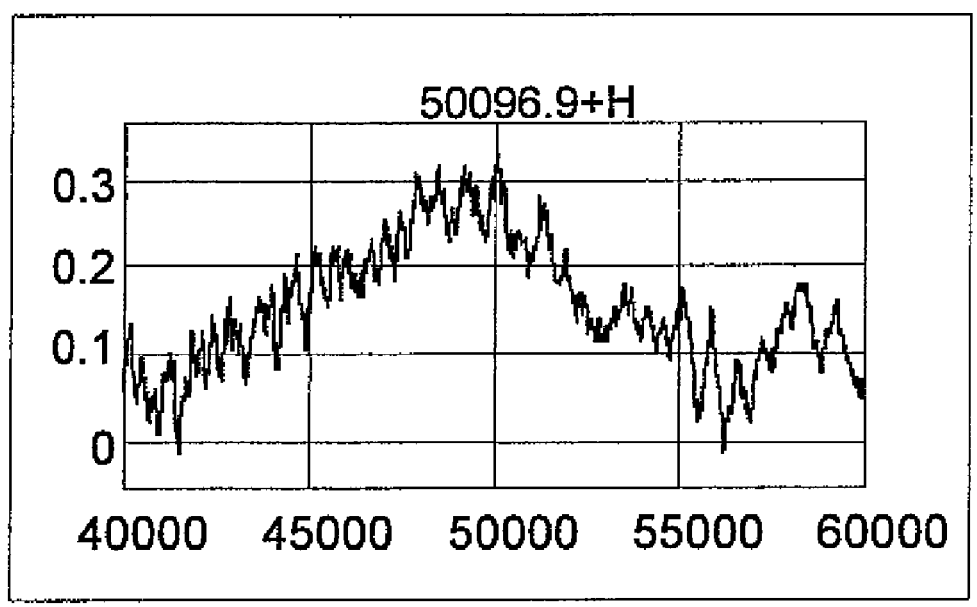
FIG. 6A shows the results for SCUPA, and FIG. 6B for HSA.
Figure 6B:
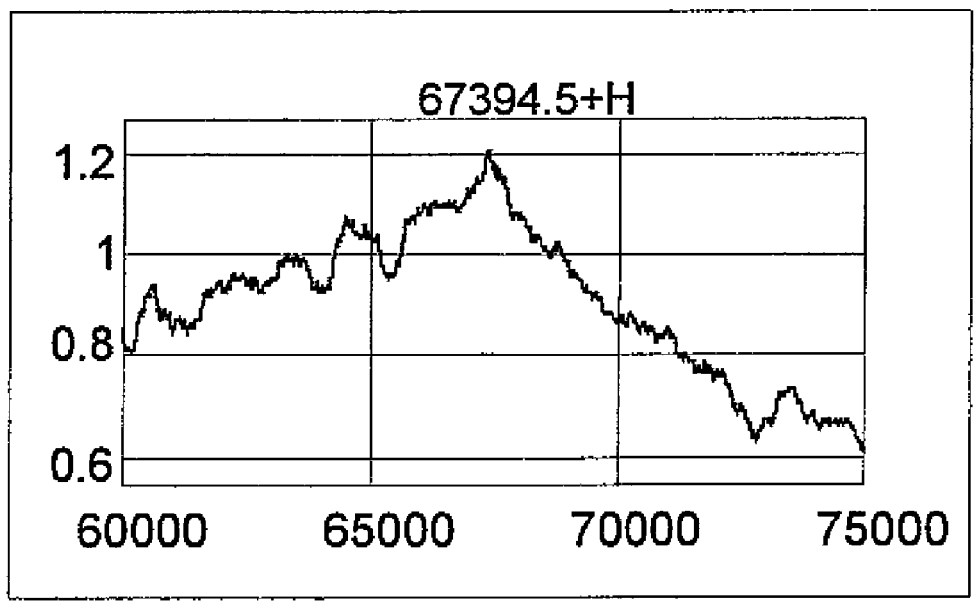
FIG. 6 shows mass spectrometry spectra obtained when electrophoresis-separated proteins were blotted to a PVDF membrane. The horizontal axis indicates molecular weight, and the vertical axis indicates relative intensity. The numerical symbols in the Figure indicate the molecular weights of the peaks.

As a result, the SCUPA blotted to the PVDF membrane produced a peak at 50,096.9, and the HSA at 67,394.5; however, the peaks were difficult to identify because the relative peak intensities were extremely low, and also because the S/N ratios were low (FIG. 6). Also, it was found that in the case of a plate for mass spectrometry (the same applies to the plate for mass spectrometry of the present invention), 2 to 3 minutes were taken to reach a high vacuum state, immediately after which measurements were possible, whereas in the case of a PVDF membrane, as long as 45 minutes were taken to reach a vacuum state, resulting in an excess load on the mass spectrometer used, and the mass spectrometer did not endure frequent use.

EXAMPLE 5

Various Proteome Analyses Using the Plate for Mass Spectrometry of the Present Invention Using various cell or tissue extraction samples, the performance of the plate for mass spectrometry of the present invention was confirmed in a range of relatively low molecular weights (molecular weight 1,000 to 20,000). In the following experiment, the sample was applied to 16% SDS-polyacrylamide gel (in Tris-Tricine buffer) and electrophoresed for 90 minutes, after which the analyte was electrically blotted from the gel to the plate for mass spectrometry of the present invention in 10 mM sodium borate buffer (adjusted to pH 8.0 with hydrochloric acid) for 1 to 2 hours. After completion of blotting, the plate was rinsed, the matrix was spotted, and mass spectrometry was conducted.

(1) A swine cerebellum was homogenized with 1N acetic acid at 4° C. and centrifuged at 4° C. and 3,000 rpm for 30 minutes, and the supernatant was recovered. Acetonitrile was added to obtain a final concentration of 10%, and the supernatant was applied to a column for reversed-phase chromatography. The column was washed with 0.1% trifluoroacetic acid (TFA) containing 10% acetonitrile, and eluted with 0.1% TFA containing 60% acetonitrile. The eluate was freeze-dried and used as the swine cerebellum extract. After this extract was separated by SDS-PAGE, it was electrically blotted to the plate for mass spectrometry of the present invention. Using 0.5% TFA/50% ACN containing saturated α-cyano-4-hydroxycinnamic acid (CHCA) as the matrix, mass spectrometry was conducted. As a result, peaks were detectable in the molecular weight range of 3,000 to 20,000.

This was compared with cases wherein DHB (150 mg/mL ethanol) or saturated SPA (in 0.5% TFA/50% ACN) was used in place of saturated CHCA as the matrix. In the case of DHB, no distinct peaks were observed in the molecular weight range of 3,000 to 20,000. In the case of saturated SPA, only several peaks were observed in the same molecular weight range. In contrast, in the case of saturated CHCA, a large number of peaks were observed in the molecular weight range of 2,000 to 10,000 and in the molecular weight range of 5,000 to 20,000. From these results, it was shown that CHCA was more preferable for identification of proteins in relatively low molecular weight ranges.

(2) Mass spectrometry of swine cerebellar extract was conducted in the same manner as (1) above except that 50% saturated CHCA was used as the matrix. As a result, peaks were detectable in the molecular weight range of 1,000 or more. In particular, excellent performance was shown in detection of peaks in the molecular weight range of 3,000 to 20,000.

This was compared with a cases using 10 or 20% saturated CHCA in place of 50% saturated CHCA, in terms of the extent of peak appearance in mass spectrometry in the molecular weight range of 1,000 to 10,000. In the case of 10% saturated CHCA, several peaks were observed. In the case of 20% saturated CHCA, the number of peaks was slightly larger than that for 10% saturated CHCA. In contrast, a large number of peaks were observed in the case of 50% saturated CHCA.

(3) U937 cells ($1 \times 10^5$ to $2 \times 10^6$ cells/ml) were cultured in a RPMI 1640 medium containing 10% FCS in the presence of 100 ng/ml phorbol 12-myristic acid ester 13-acetic acid salt (PMA) for 48 hours. The same experiment, but in the absence of PMA, was conducted for control. After completion of cultivation, the cells were washed with phosphate-buffered saline (PBS), and cell pellets were prepared. Furthermore, a protein extraction reagent (Novagen Inc.) and a protease inhibitor were added, and the pellets were allowed to stand at 4° C. for 15 minutes, after which they were centrifuged, and the supernatant was recovered and used as the cell lysate. After this was separated by SDS-PAGE, it was electrically blotted to the plate for mass spectrometry of the present invention. Subsequently, mass spectrometry was conducted;

in terms of the intensities of the peaks detected in the molecular weight range of 3,000 to 20,000, the results for the PMA-stimulated U937 cells were compared with the results for the control U937 cells. As a result, the following changes in the PMA-stimulated expression of proteins (peak intensity) were observed (Table 1).

TABLE 1

| Changes in peak (intensity) | Peak number |
| --- | --- |
| Disappeared | 38 |
| Appeared | 11 |
| Decreased | 1 |
| Increased | 2 |

(4) Profiling of mouse tissues was conducted. Mouse tissues (brain, lung, liver, muscle) were disrupted by treatment using the Beads Shocker (Yasui Kikai Corporation, Osaka) at 2,500 rpm for 10 to 30 seconds, TricinePAGE sample buffer (Wako Pure Chemical Industries) was added, centrifugation was conducted at 12,000 rpm for 5 minutes, and the supernatant was recovered. After separation by SDS-PAGE, the supernatant was electrically blotted to the plate for mass spectrometry of the present invention, and mass spectrometry was conducted. As a result, a tissue-specific peptide (molecular weight 3,000 to 20,000) was detected in each tissue.

EXAMPLE 6

Investigation of Effects of Buffer at the Time of Electrical Blotting

As the buffer at the time of electrical blotting, a Tris buffer (25 mM Tris/192 mM glycine/20% methanol, pH 8.3), a phosphate buffer (5% ACN/125 mM NaCl/PBS, pH 7.2), an acetate buffer (40 mM Tris-acetate salt/1 mM EDTA, pH 8.0), and a borate buffer (10 mM sodium borate-hydrochloric acid, pH 8.0) were used. As the proteins for mass spectrometry, HSA and SCUPA were used. Except for these conditions, an experiment was conducted in accordance with the method of Example 5. As a result, of the buffers examined, the borate buffer gave the maximum mass spectrometry peak intensity. For example, the ratio of maximum value of peak intensity for the borate buffer versus the phosphate buffer was about 21 times for SCUPA and about 4 times for HSA.

INDUSTRIAL APPLICABILITY

Owing to the use of PVDF as the ligand adsorbent, the plate for mass spectrometry of the present invention is capable of uniformly adsorb various proteins, is excellent in blotting efficiency, and enables the normal retention of the three-dimensional structures and functions of the proteins. The plate for mass spectrometry of the present invention is also characterized by the absence of non-specific adsorption, the capability of performing mass spectrometry immediately after blotting, and the like.

Making use of these features of the plate for mass spectrometry of the present invention, a protein can be analyzed and identified in large amounts, with quickness, and at high sensitivity. The protein may be of one kind, or an assembly of a plurality of kinds (a group of proteins), and even a complex with a compound that has affinity for (interacts with) the protein can be analyzed and identified likewise (that is, in large amounts, with quickness, and at high sensitivity).

Also, significant shortening of operating time, step simplification, apparatus size reduction, price reduction, automation, and screening of a large number of analytes are enabled, and large-scale proteome analysis is facilitated. Furthermore, proteome analysis of physiologically important low-abundance proteins is enabled, thus contributing to the discovery of biomarkers for diagnostic use and the discovery of seed compounds for new drug development.

Therefore, the present invention makes it possible to introduce a new technique to the conventional proteome analysis, which is a combination of electrophoresis and mass spectrometry.

The present application is based on U.S. application Ser. No. 10/264,505 filed in the United States and Japanese Patent Application No. 2002-344710 filed in Japan, the teachings of which are included in their entirety in the present specification.

All citations, including the publications and patents mentioned herein, are incorporated in the specification, by being cited herein, to the same extent that they are individually shown to be incorporated by reference and all of them are specified herein.

Although the present invention has been described with emphasis on preferred embodiments, it is obvious to those skilled in the art that the preferred embodiments may be modified. The present invention may be embodied by methods other than those described in detail herein. Therefore, the present invention includes all modifications encompassed in the spirit and scope of the attached claims.

The invention claimed is:

1. A method of identifying an analyte, comprising:
   (a) providing a plate for mass spectrometry comprising a support and a polyvinylidene difluoride coating adhering thereto, wherein the plate for mass spectrometry is prepared by the following steps:
      (i) providing a support and
      (ii) depositing polyvinylidene difluoride molecules in dispersion on the support, thereby forming a polyvinylidene difluoride coating on the support,
   (b) subjecting an analyte-containing sample to gel electrophoresis, thereby forming a gel containing the analyte,
   (c) blotting the gel containing the analyte to the plate to transfer the analyte to the plate,
   (d) contacting the plate with a sample containing a substance that has affinity for the transferred analyte to form a complex of the transferred analyte and the substance on the plate,
   (e) adding a matrix for mass spectrometry to the plate, and
   (f) subjecting the plate to mass spectrometry to simultaneously analyze the transferred analyte and the substance.

2. The method of claim 1, wherein the blotting is electrical blotting.

3. The method of claim 1, wherein the mass spectrometry is MALDI-MS.

4. The method of claim 1, wherein the analyte-containing sample contains a plurality of kinds of analytes.

5. The method of claim 1, wherein the analyte is selected from the group consisting of protein, nucleic acid, oligonucleotide, saccharide, oligosaccharide, cell membrane receptor agonist or antagonist, toxin, virus epitope, hormone, peptide, enzyme, enzyme substrate or inhibitor, cofactor, drug, lectin and antibody.

6. The method of claim 1, wherein the matrix is 2,5-dihydroxybenzoic acid.

7. The method of claim 1, wherein the support is made of aluminum or stainless steel.

8. The method of claim 1, wherein depositing polyvinylidene difluoride molecules in dispersion on the support is carried out by painting, spraying, vapor deposition, immersion, printing, or sputtering.

9. The method of claim 1, wherein depositing polyvinylidene difluoride molecules in dispersion on the support is carried out by applying a solution containing polyvinylidene difluoride and a solvent therefor to the support.

10. The method of claim 9, wherein the solvent is removed after application of the solution to the support.

* * * * *